US00PP11447P

United States Patent [19]

Boeder

[11] Patent Number: Plant 11,447

[45] Date of Patent: Jul. 18, 2000

[54] CHRYSANTHEMUM PLANT NAMED 'TRENDY TIME'

[75] Inventor: Mark Boeder, West Wittering, United Kingdom

[73] Assignee: Cleangro Limited, West Sussex, United Kingdom

[21] Appl. No.: 09/082,266

[22] Filed: May 20, 1998

[51] Int. Cl.[7] ..... A01H 5/00

[52] U.S. Cl. ..... Plt./295

[58] Field of Search ..... Plt./295

*Primary Examiner*—Howard J. Locker
*Attorney, Agent, or Firm*—Christie, Parker & Hale, LLP

[57] ABSTRACT

A new variety of chrysanthemum producing large yellow daisy-type flowers with spoon-type ray florets, suitable for potted plant production.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'Trendy Time'.

The female parent of the new variety is an undistributed, unnamed variety identified as P110-90, and the male parent is an undistributed, unnamed seedling identified as P11-90. The new variety has been asexually reproduced by vegetative cuttings in Ventura County, Calif. and the distinguishing characteristics are retained through successive generations of asexual reproduction.

SUMMARY OF THE INVENTION

'Trendy Time' is pot type chrysanthemum plant variety that produces large, daisy-type flowers with spoon-type ray florets, suitable for potted plant production.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of November. 'Trendy Time' has been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once with center bud removed for spray, or lateral bud removed for disbud-type plants. It has been observed that the shelf life of 'Trendy Time' is about 27 days with the response time of about 9 weeks. One treatment with growth regulator B-9 at 2000 ppm is useful. Desirable growing conditions include average night temperatures of about 64°–66° F. day temperatures of about 75°–85° F. and about 5,000–6,000 foot-candles of light.

Plant:

*Habit.*—Upright.
*Height.*—About 31 cm.
*Number of breaks from pinch.*—About 3.

*Typical container sizes commercially grown in.*—6 inch and 8 inch pots.
*Length of lateral branches.*—About 25 cm.
*Stem color.*—Near 146D.

Foliage:

*Leaf Arrangement.*—Alternate.
*Number of leaves per lateral branch.*—About 10.
*Leaf size.*—*Length: About* 8.2 cm. Width: About 5.2 cm.
*Leaf shape.*—Ovate.
*Attachment.*—Petioled.
*Leaf apex.*—Acute.
*Base.*—Tapered.
*Margin.*—Lobed, infrequent dentations.
*Aspect.*—flat.
*Surface.*—Top: Slightly pubescent. Bottom: Pubescent.
*Venation.*—Net, prominent mid vein on underside; mid vein color underside near 137D, upper side near 146C.
*Petiole length.*—About 2.4 cm. Color: Near 144A.
*Stipule characteristics.*—Two present at each leaf; irregular shapes and sizes.
*Color.*—Mature leaf: Top: Near 137A. Bottom: Near 138B. Young leaf: Top: Near 137A. Bottom: Near 137C.

Flower:

*Inflorescence form.*—Cyme.
*Flower form.*—Daisy-type.
*Number of blooms per branch.*—About 6.
*Diameter of fully expanded bloom.*—About 8.2 cm.
*Diameter of disc.*—About 2 cm.
*Depth of fully expanded bloom.*—About 1.5 cm.
*Sepal number.*—About 40. Color: Near 137A.
*General appearance of sepals.*—Highly membranous and pubescent.
*Peduncle.*—Length: Longest about 9 cm, terminal peduncle about 3 cm. Habit: Straight. Surface: Pubescent. Strength: Soft.
*Flower bud shape.*—Flattened sphere. Diameter: About 1.2 cm. Height: About 0.9 cm.
*Ray florets.*—Number per flower: About 48. Shape: Spoon. Apex: Obtuse lobes. Base: Fused. Margin: Entire. Aspect: Straight with slight reflex at tip. Length: About 4 cm. Width: About 0.7 cm.
*Disc florets.*—Number per flower: About 250. Shape: Cylindrical. Margin: Entire. Length: About 0.5 cm. Width: About 0.1 cm.
*Fragrance.*—Very faint.

Flower color:

*General flower coloration.*—Bright yellow daisy with spoon tipped petals; green disc before mature.

*Ray florets, top side.*—Immature: Near 9A. Mature: Near 9A. Fading: Near 9B.

*Ray floret, under side.*—Immature: Near 7B. Mature: Near 12B. Fading: Near 9C.

*Disc florets.*—Immature: Near 154B. Mature: Near 15A. Fading: Near 17C.

*Changes as the flower ages.*—Disc turns from yellow-green to yellow-orange; ray petals maintain color.

Reproductive organs:

*Ray florets.*—Pistillate. Stigma shape: 2 or 3 branched. Stigma color: Near 13B. Style length: About 0.6 cm.

*Disc florets.*—Stigma shape: 2 branched. Stigma color: Near 14B. Style Length: About 0.6 cm. Stamen number: About 5. Anther length: About 0.2 cm. Pollen color: Near 14A. Pollen quantity: Moderate.

What is claimed is:

1. A new and distinct chrysanthemum plant of the variety substantially as herein shown and described.

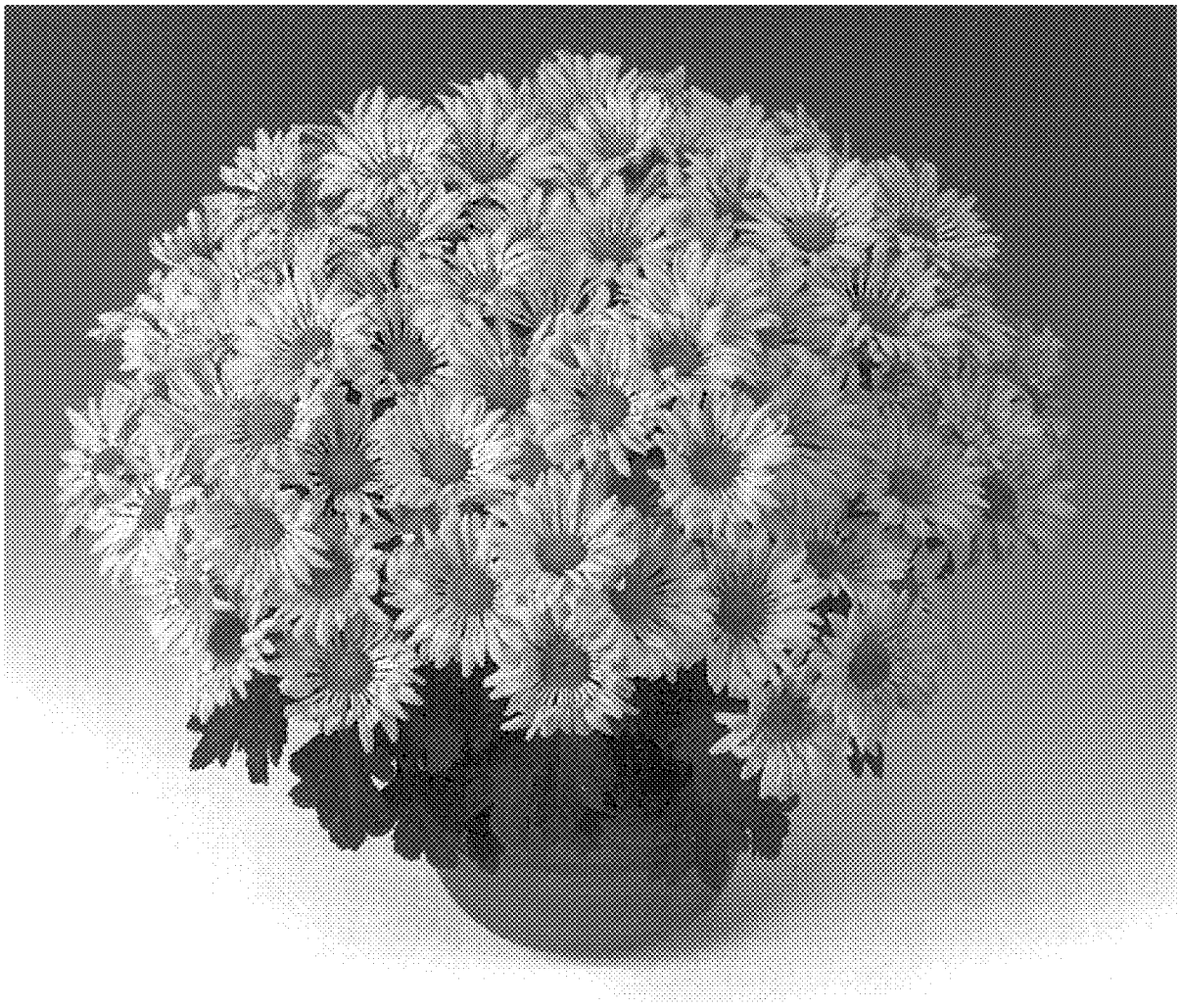

* * * * *